US009199900B2

(12) United States Patent
Siewert et al.

(10) Patent No.: US 9,199,900 B2
(45) Date of Patent: Dec. 1, 2015

(54) METHOD FOR CONVERTING FARNESOL TO NEROLIDOL IN THE PRESENCE OF ALPHA-BISABOLOL

(71) Applicant: Symrise AG, Holzminden (DE)

(72) Inventors: Jürgen Siewert, Rollshausen (DE); Burghard Wilkening, Bodenwerder (DE)

(73) Assignee: Symrise AG, Holzminden (DE)

( * ) Notice: Subject to any disclaimer, the term of this patent is extended or adjusted under 35 U.S.C. 154(b) by 120 days.

(21) Appl. No.: 13/866,119

(22) Filed: Apr. 19, 2013

(65) Prior Publication Data

US 2013/0289317 A1 Oct. 31, 2013

(30) Foreign Application Priority Data

Apr. 27, 2012 (EP) ..................................... 12165873

(51) Int. Cl.
*C07C 29/56* (2006.01)
*C07C 33/02* (2006.01)
*C07C 29/88* (2006.01)
*C07C 33/14* (2006.01)

(52) U.S. Cl.
CPC ................. *C07C 29/56* (2013.01); *C07C 29/88* (2013.01); *C07C 33/14* (2013.01)

(58) Field of Classification Search
CPC ....................................................... C07C 29/56
See application file for complete search history.

(56) References Cited

U.S. PATENT DOCUMENTS

| 4,006,193 A | 2/1977 | Ninagawa et al. |
| 6,566,564 B1 | 5/2003 | Ebel et al. |
| 6,989,468 B2 | 1/2006 | Haese et al. |
| 7,399,880 B2 | 7/2008 | Betzer et al. |
| 2008/0269530 A1 | 10/2008 | Massonne et al. |

FOREIGN PATENT DOCUMENTS

| DE | 2516698 A1 | 10/1975 |
| DE | 2557837 A1 | 6/1976 |
| DE | 10046865 A1 | 3/2002 |
| DE | 102005026768 A1 | 12/2006 |
| DE | 102005051903 A1 | 5/2007 |
| DE | 102005053338 A1 | 5/2007 |
| EP | 0585680 A1 | 3/1994 |
| GB | 1256184 A | 12/1971 |
| GB | 1479272 A * | 7/1977 |
| WO | 2004/033401 A1 | 4/2004 |
| WO | 2007/082847 A1 | 7/2007 |
| WO | 2008098774 A1 | 8/2008 |

OTHER PUBLICATIONS

DE102005053338, May 10, 2007, pp. 1-14; English translation.*
DE102005026768, Dec. 21, 2006, pp. 1-5; English translation.*
WO2004/033401, Apr. 22, 2004, pp. 1-7; English translation.*
European Patent Search Report dated Oct. 10, 2012 for priority application EP 12165873.6.

* cited by examiner

*Primary Examiner* — Fereydoun G Sajjadi
*Assistant Examiner* — Medhanit Bahta
(74) *Attorney, Agent, or Firm* — Dilworth & Barrese, LLP

(57) ABSTRACT

A method for converting farnesol to nerolidol in the presence of alpha-bisabolol including providing or preparing a mixture of alpha-bisabolol, farnesol, and one or more catalysts for selective isomerization of farnesol to nerolidol in the presence of alpha-bisabolol, and converting at least a portion of the farnesol to nerolidol.

31 Claims, No Drawings

METHOD FOR CONVERTING FARNESOL TO NEROLIDOL IN THE PRESENCE OF ALPHA-BISABOLOL

CROSS-REFERENCE TO RELATED APPLICATIONS

This application claims the benefit of EP Patent Application Serial No. 12 165 287.9, filed on 27 Apr. 2012, the benefit of the earlier filing date of which is hereby claimed under 35 USC §119(a)-(d) and (f). The application is hereby incorporated in its entirety as if fully set forth herein.

BACKGROUND OF THE INVENTION

1. Field of the Invention

The present invention relates to a method for converting farnesol to nerolidol in the presence of alpha-bisabolol. Thus, the present invention relates to a method of depletion of farnesol from mixtures containing farnesol and alpha-bisabolol.

2. Description of Related Art

Natural alpha-bisabolol is an important constituent of the essential oil of the chamomile species *Chamomilla recutita*. Alpha-bisabolol is used in cosmetic and pharmaceutical applications owing to its skin-calming and anti-inflammatory properties. Furthermore, alpha-bisabolol is used as an odoriferous substance in the perfume industry.

Whereas the systematic cultivation of medicinal and spice plants such as chamomile is becoming increasingly important owing to a growing demand for "renewable raw materials", the limited natural resources have at the same time led to the search for and development of methods of producing synthetic products.

Synthetic "alpha-bisabolol" is usually a diastereomeric racemate of equal proportions of (+/−)-alpha-bisabolol and (+/−)-epi-alpha-bisabolol. These four enantiomers (+)-epi-alpha-bisabolol, (−)-alpha-bisabolol, (+)-epi-alpha-bisabolol, (−)-epi-alpha-bisabolol possess a structure according to formula A

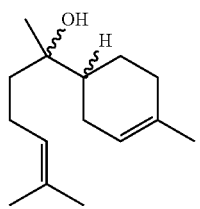

A in which wavy lines stand, in each case independently of one another, for an S- or R-configuration on the associated carbon atom. The compounds of formula A are designated together in the present text with the term alpha-bisabolol.

Owing to their structural similarity to alpha-bisabolol, the sesquiterpenes nerolidol (formula B) and farnesol (formula C), in which wavy lines stand in each case independently of one another for an S- or R-configuration on the associated carbon atom, present themselves as starting materials for industrial synthesis.

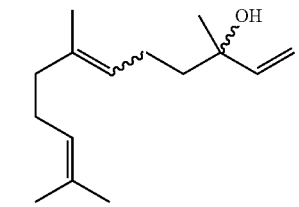

B

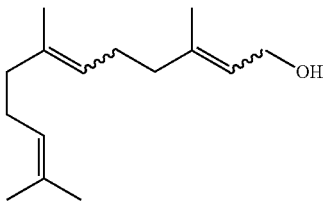

C

Thus, a great many methods and processes have been described in the past for the production of alpha-bisabolol starting from nerolidol or farnesol.

The first catalytic cyclization of farnesol was described in 1913, when it was observed that on carrying out a reaction in the presence of potassium hydrogen sulfate, in addition to the expected hydrocarbons, some mono- and bicyclic compounds were also found [Chem. Ber. 46, 4024 (1913)]. Later works then identified these cyclic compounds as compounds of the bisabolene and cadalene class.

In 1925 it was shown for the first time that starting from nerolidol, by acid catalysis, products such as farnesene, bisabolene and alpha-bisabolol are obtained [Hely. Chim. Acta 8, 259 (1925)]. It was shown, in particular, that by adding acetic anhydride, then reacting with acetic acid/sulfuric acid or formic acid at room temperature, followed by saponification, nerolidol yields a mixture that comprises alpha-bisabolol and farnesol.

In 1968, Gutsche reported [Tetrahedron 24, 859] on the acid-catalyzed cyclization of farnesol and nerolidol. Starting from farnesol or nerolidol, first by reacting with formic acid, the corresponding formates were obtained, which were then saponified in a second step to the alcohols. Following this procedure, however, mixtures of substances are formed, which contain farnesol as well as alpha-bisabolol. Subsequent purification by distillation to highly-enriched alpha-bisabolol proves difficult, especially because alpha-bisabolol and cis,cis-farnesol have almost identical boiling points and the mixtures of substances obtained by the procedure described contain up to 10% of cis,cis-farnesol.

Further syntheses of alpha-bisabolol were described by Ruzicka et al. [Hely. Chim. Acta 15, 3, (1932)] and by Manjarrez et al. [J. Org. Chem. 31, 348, (1966)]. The acid-catalyzed cyclization in the presence of formic acid in pentane or $AlCl_3$ in ether [Tetrahedron Lett. 1972, 2455], $KHSO_4$ [J. Org. Chem. 34, 3789, (1969)] and $BF_3$-etherate in methylene chloride [Chem. Lett. 1972, 263] was also described.

Uneyama et al. report on an electrochemical method of preparation [Chem. Lett. 1984, 529], and the production of DL-bisabolol from DL-nerolidol is also reported. Whereas the methods presented previously, starting from nerolidol, rarely led to alpha-bisabolol yields over 30%, with electrochemical methods yields of up to 52% were obtained.

WO 2004/033401 discloses a method of producing alpha-bisabolol, in which nerolidol is reacted in a step with a mixture consisting of a ketone, a sulfonic acid and perchloric acid. This method is characterized in that, among other things, it leads to an especially pure alpha-bisabolol and in particular the (+), (−) or (+/−)-farnesol that formed as a by-product in the methods described previously in a yield of up to 40%, only formed in relatively low concentrations. However, the use of perchloric acid is problematic on grounds of safety.

The use of perchloric acid, which is critical from the standpoint of safety, is avoided in the method known from DE 10 2005 053 338 for production of alpha-bisabolol, comprising the reaction of farnesol or nerolidol or mixtures of farnesol and nerolidol in the presence of a ketone, a sulfonic acid and another strong acid, except perchloric acid.

US 2008/0269530 A1 discloses a method of producing alpha-bisabolol, comprising the reaction of farnesol in the presence of a ketone, a sulfonic acid and another strong acid. The resulting product mixture contains alpha-bisabolol and its dehydration products as main components. After working up the reaction mixture, farnesol is still only present in low concentrations.

Syntheses starting from farnesol supply the desired alpha-bisabolol, but only in lower yields compared to the syntheses starting from nerolidol.

A feature that the known methods of production of alpha-bisabolol have in common is that farnesol is also formed regularly, in varying amounts. However, the presence of farnesol in product mixtures along with alpha-bisabolol is undesirable, because farnesol is described as having allergenic potential, which in particular makes its use in cosmetic products problematic. In the development of cosmetic products, not only the cosmetic properties are of interest—it is of course also necessary to ensure that the ingredients are harmless to people and the environment. Improved toxicological, ecotoxicological and dermatological properties contribute to the value of a new product. Dermatologically, a cosmetic product should not have any skin-irritant, sensitizing and/or photosensitizing properties. In that sense, the presence of farnesol in cosmetic products is increasingly being perceived as problematic.

It was mentioned above that the separation of alpha-bisabolol and farnesol by distillation is difficult in particular because alpha-bisabolol and cis,cis-farnesol have almost identical boiling points. If it is nevertheless necessary for product mixtures that also comprise a notable proportion of farnesol along with the desirable alpha-bisabolol to be separated by distillation, attainment of at least a certain level of success requires such long thermal loading that there is considerable occurrence of side reactions and especially decomposition of the previously synthesized compounds. In addition, the conventional separation of alpha-bisabolol and farnesol by distillation only gives farnesol of low purity, which is not suitable for direct further use, and especially not as an educt for the synthesis of alpha-bisabolol.

The removal of farnesol from mixtures with alpha-bisabolol by esterification is described in U.S. Pat. No. 7,399,880 B2. The method avoids the problem of separation by distillation, by selective transesterification of the farnesol contained in the mixture with a carboxylic acid ester in the presence of a transesterification catalyst. The farnesyl esters thus obtained now have boiling points that are markedly different from those of alpha-bisabolol, and can be separated by simple distillation. With this method, product mixtures containing alpha-bisabolol can be achieved with farnesol contents below 0.5%.

The selective esterification of farnesol is achieved, according to DE 10 2005 026 768, by reaction of the farnesol contained in the mixture with a nitrogen base and a benzoyl halide. The corresponding farnesyl benzoates are formed selectively, and can be separated in a simple distillation step.

In US 2010/0222606 A1 (WO 2007/082847), the problem of separating farnesol and alpha-bisabolol is also solved by esterification of the farnesol. The method is characterized in particular in that no wastewater is formed. The farnesyl carboxylic acid esters formed as coupling product can be used e.g. in fragrance applications, or in an alternative step they can be converted by saponification to farnesol. In this case, however, process wastewater is formed. The resultant farnesol can be used as educt for producing alpha-bisabolol.

BRIEF SUMMARY OF THE INVENTION

The problem to be solved by the present intention is to provide a method that allows selective reaction of farnesol in the presence of alpha-bisabolol, so that a product mixture containing alpha-bisabolol can be obtained that is largely or essentially free from farnesol. Preferably the farnesol should be converted to a product that can in its turn be converted easily, with good yields, to alpha-bisabolol.

In an exemplary embodiment, the present invention comprises a method of converting farnesol to nerolidol in the presence of alpha-bisabolol comprising providing or preparing a mixture of alpha-bisabolol, farnesol, and one or more catalysts for selective isomerization of farnesol to nerolidol in the presence of alpha-bisabolol, and converting at least a portion of the farnesol to nerolidol.

The process conditions can be selected so that after farnesol has been converted to nerolidol, the molar ratio of alpha-bisabolol to farnesol is greater than in the mixture that was prepared or provided.

In the mixture that was prepared or provided, the molar ratio of alpha-bisabolol to farnesol can be in a range from 15:1 to 1:100, preferably 2:1 to 1:2.

The process conditions can be selected so that after farnesol has been converted to nerolidol, the molar ratio of alpha-bisabolol to farnesol is 30:1 or higher, preferably 50:1 or higher, more preferably 80:1 or higher, especially preferably 100:1 or higher.

One or more of the catalysts for selective isomerization of farnesol to nerolidol in the presence of alpha-bisabolol can comprise a compound of a transition metal of groups 5 to 8 of the periodic table, preferably a compound of a transition metal selected from the group consisting of vanadium, rhenium, tungsten, manganese, chromium, molybdenum and palladium.

One or more of the catalysts for selective isomerization of farnesol to nerolidol in the presence of alpha-bisabolol can comprise a compound selected from the group consisting of vanadic acid and esters and ammonium salts thereof, preferably selected from the group consisting of vanadium(III) acetylacetonate, vanadyl(IV) acetylacetonate, vanadium(V) oxytriisopropoxide and ammonium metavanadate.

One or more of the catalysts for selective isomerization of farnesol to nerolidol in the presence of alpha-bisabolol can comprise chelates and organometallic compounds of the transition metals of groups 5 to 8 of the periodic table, preferably chelates and organometallic compounds of the transition metals selected from the group consisting of vanadium, rhenium, tungsten, manganese, chromium, molybdenum and palladium, preferably selected from the group of oxoperoxotungsten(VI) complexes comprising one or more ligands in the form of 8-hydroxyquinoline.

The mixture that was prepared or provided can contain 0.0001 to 1 mol, preferably 0.001 to 0.5 mol, of transition metal per mol of farnesol, relative to the amount of farnesol present in the mixture that was prepared or provided.

The conversion of farnesol to nerolidol can be carried out at a temperature in the range from 50 to 300° C., preferably in the range from 150 to 200° C. and/or wherein the conversion of farnesol to nerolidol can be carried out at a pressure of less than 1000 mbar, preferably in the range from 0.1 to 500 mbar.

The mixture can contain one or more additional constituents selected from the group consisting of: nerolidol, elimination products of alpha-bisabolol, elimination products of farnesol, elimination products of nerolidol, etherification products of farnesol, further sesquiterpenes, sesquiterpene alcohols, germacradienol, beta-bisabolol, further rearrangement products of alpha-bisabolol, nerolidol and farnesol, and other solvents.

The step of preparing the mixture can comprise the conversion of at least a portion of nerolidol to a mixture comprising alpha-bisabolol and farnesol.

During and/or after conversion of at least a portion of farnesol to nerolidol, alpha-bisabolol and nerolidol can be separated from one another, preferably wherein during and/or after conversion of at least a portion of farnesol to nerolidol, the nerolidol can be separated by distillation from the mixture obtained by conversion of at least a portion of farnesol to nerolidol.

The steps of the method can be carried out in the same reaction vessel.

The step of providing or preparing the mixture can comprise saponification of alpha-bisabolyl formate and farnesyl formate mixed together or transesterification of alpha-bisabolyl formate and farnesyl formate mixed together with an alcohol.

The catalyst can be dissolved in the mixture that is prepared or provided or can be suspended in the mixture that is prepared or provided, wherein in this case the catalyst preferably comprises a support.

The present invention can further comprise the use of a catalyst comprising a compound of a transition metal of groups 5 to 8 of the periodic table, preferably a compound of a transition metal selected from the group consisting of vanadium, rhenium, tungsten, manganese, chromium, molybdenum and palladium for selective isomerization of farnesol to nerolidol in the presence of alpha-bisabolol.

DETAILED DESCRIPTION OF THE PREFERRED EMBODIMENTS

To facilitate an understanding of the principles and features of the various embodiments of the invention, various illustrative embodiments are explained below. Although exemplary embodiments of the invention are explained in detail, it is to be understood that other embodiments are contemplated. Accordingly, it is not intended that the invention is limited in its scope to the details of construction and arrangement of components set forth in the following description or illustrated in the drawings. The invention is capable of other embodiments and of being practiced or carried out in various ways. Also, in describing the exemplary embodiments, specific terminology will be resorted to for the sake of clarity.

It must also be noted that, as used in the specification and the appended claims, the singular forms "a," "an" and "the" include plural references unless the context clearly dictates otherwise. For example, reference to a component is intended also to include composition of a plurality of components. References to a composition containing "a" constituent is intended to include other constituents in addition to the one named.

Also, in describing the exemplary embodiments, terminology will be resorted to for the sake of clarity. It is intended that each term contemplates its broadest meaning as understood by those skilled in the art and includes all technical equivalents which operate in a similar manner to accomplish a similar purpose.

Ranges may be expressed herein as from "about" or "approximately" or "substantially" one particular value and/or to "about" or "approximately" or "substantially" another particular value. When such a range is expressed, other exemplary embodiments include from the one particular value and/or to the other particular value.

Similarly, as used herein, "substantially free" of something, or "substantially pure", and like characterizations, can include both being "at least substantially free" of something, or "at least substantially pure", and being "completely free" of something, or "completely pure".

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

It is also to be understood that the mention of one or more method steps does not preclude the presence of additional method steps or intervening method steps between those steps expressly identified. Similarly, it is also to be understood that the mention of one or more components in a composition does not preclude the presence of additional components than those expressly identified.

The materials described as making up the various elements of the invention are intended to be illustrative and not restrictive. Many suitable materials that would perform the same or a similar function as the materials described herein are intended to be embraced within the scope of the invention. Such other materials not described herein can include, but are not limited to, for example, materials that are developed after the time of the development of the invention.

The present invention preferably comprises a method of converting farnesol to nerolidol in the presence of alpha-bisabolol by:
  providing or preparing a mixture comprising:
    alpha-bisabolol;
    farnesol;
    one or more catalysts for selective isomerization of farnesol to nerolidol in the presence of alpha-bisabolol; and
    optionally further constituents; and
  converting farnesol to nerolidol in the mixture.

The term "alpha-bisabolol" comprises, in the context of this text, (+)-alpha-bisabolol, (−)-alpha-bisabolol, (+)-epi-alpha-bisabolol and (−)-epi-alpha-bisabolol and mixtures of two, three or all of the stated isomers of alpha-bisabolol. In particular the term "alpha-bisabolol" comprises racemic mixtures of (+/−)-alpha-bisabolol and/or (+/−)-epi-alpha-bisabolol.

The term "farnesol" comprises, in the context of this text, the cis/cis, the cis/trans, the trans/cis and the trans/trans isomer and mixtures of two, three or all of the stated isomers of farnesol.

The invention is based on the surprising finding that the farnesol contained in the mixture prepared or provided, comprising alpha-bisabolol, farnesol and optionally further constituents can, in the presence of a suitable catalyst, be converted selectively to nerolidol (boiling point 145 to 146° C. at 16 mbar), which can easily be separated by distillation from the alpha-bisabolol. At the end of the reaction a product mixture is at hand comprising alpha-bisabolol, nerolidol and a reduced proportion of farnesol relative to the mixture that was prepared or provided.

According to the invention, the process conditions are preferably selected in such a way that after farnesol has been converted to nerolidol the molar ratio of alpha-bisabolol to farnesol is greater than in the mixture that was prepared or provided.

In the mixture that was prepared or provided, the molar ratio of alpha-bisabolol to farnesol is preferably in a range from 15:1 to 1:100, preferably 2:1 to 1:2. The molar ratio and the respective amount of substance in the mixture can be determined for example by gas chromatography, and for precise determination an internal standard should be used. Unless stated otherwise below, this method of determination is to be used.

In the absence of an internal standard, the GC area ratio can be compared and can be equated with the molar ratio; usually this produces a slight error, but in industrial practice this can be neglected or is acceptable.

Preferably, according to the invention, the process conditions are selected in such a way that after farnesol has been converted to nerolidol the molar ratio of alpha-bisabolol to farnesol is 30:1 or higher, preferably 50:1 or higher, more preferably 80:1 or higher, especially preferably 100:1 or higher. Preferred configurations of the method according to the invention are preferably combined with one another.

The catalytic reaction, according to the invention, of farnesol (C) to nerolidol (B) in the presence of alpha-bisabolol (A), which itself is not reacted or is reacted but only to a slight extent, together with the distilling-off of the nerolidol that is preferred according to the invention, is shown simplified in the following scheme 1. It is to be understood that the isomers of alpha-bisabolol, of farnesol and of nerolidol shown are only examples.

Scheme 1

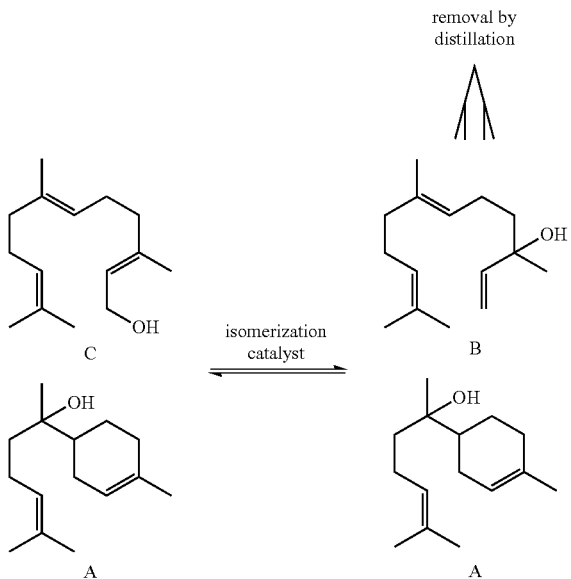

The rearrangement of higher allyl alcohols is, owing to the varied uses of these allyl alcohols, e.g. in the production of plasticizer alcohols or of vitamins A and E, an economically important field, especially as the acid-catalyzed rearrangement often only takes place with poor yields. Various approaches are therefore adopted in the prior art, which primarily involve the isomerization of tertiary allyl alcohols to the primary or secondary allyl alcohols, especially the isomer pair linalool and neroligeraniol.

GB 1 256 184 (U.S. Pat. No. 3,925,485) discloses the isomerization of allyl alcohols using catalytic amounts of transition metal compounds of groups 5, 6 and 7. Vanadium compounds are preferred. Examples of the use of compounds of other elements are not given.

U.S. Pat. No. 4,006,193 discloses the use of compounds of transition metals of groups 5, 6 and 7. Once again, the vanadium compounds are preferred, because compared with molybdenum, rhenium and chromium compounds, these give much better yields and selectivities. The isomerization of farnesol to nerolidol by distillation is presented as an example.

DE 25 16 698 discloses the use of improved tungsten complexes. The complexes have silanol groups and a nitrogen-containing base as ligands.

In the academic literature, the aforementioned catalyst systems were described in Chem. Lett. 1982, 357-360 and Tetrahedron 1977, 33, 1775-1783.

As well as the catalyzed allyl rearrangements with complexes and compounds of transition metals of groups 5, 6 and 7 already described, DE 25 57 837 additionally discloses the possibility of using compounds of group 8 transition metals and the possibility of allyl rearrangement using a catalyst system consisting of an organic or inorganic sulfur compound and a radical initiator.

EP 0 585 680 (U.S. Pat. No. 5,349,097) relates to allyl rearrangement using rhenium compounds. Using organo-rhenium catalysts, e.g. methyltrioxorhenium (MTO), much better results were achieved compared to the rhenium compounds described up to now.

DE 100 46 865 discloses the use of a peroxotungsten complex as catalyst for the isomerization of allyl alcohols. Comparable to DE 25 16 698, once again a nitrogen base, especially 8-hydroxyquinoline, is used as ligand.

WO 2008/098774 discloses a combination of a transition metal, the oxidant TEMPO (2,2',6,6'-tetramethylpiperidin-1-oxyl) and a co-oxidant as an effective catalyst for the allyl rearrangement.

Further catalysts for the isomerization of allyl alcohols are known from U.S. Pat. No. 6,566,564 and U.S. Pat. No. 6,989,468.

Preferably, in methods according to exemplary embodiments of the invention, one, several or all of the catalysts for selective isomerization of farnesol to nerolidol in the presence of alpha-bisabolol comprise a compound of a transition metal of groups 5 to 8 of the periodic table, preferably a compound of a transition metal selected from the group consisting of vanadium, rhenium, tungsten, manganese, chromium, molybdenum and palladium. It was found in our own research that such catalysts, when added to a mixture comprising alpha-bisabolol and farnesol, convert the farnesol selectively to nerolidol, whereas the alpha-bisabolol is stable under the reaction conditions, or is only slightly reacted or decomposed.

Especially preferably, in the method according to the invention, one, several or all of the catalysts for selective isomerization of farnesol to nerolidol in the presence of alpha-bisabolol are selected from the group consisting of:
vanadic acid and esters and ammonium salts thereof,
chelates and organometallic compounds of the transition metals of groups 5 to 8 of the periodic table, preferably chelates and organometallic compounds of the transition metals selected from the group consisting of vanadium, rhenium, tungsten, manganese, chromium, molybdenum and palladium.

Esters $(VO(OR^1)(OR^2)(OR^3))$ of orthovanadic acid and chelates $(VO(R^4(C\!=\!O)CH(C\!=\!O)R^5)_2)$ of tetravalent vanadium and chelates $(V(R^4(C\!=\!O)CH(C\!=\!O)R^5)_3)$ of trivalent vanadium are especially preferred, wherein $R^1$, $R^2$, $R^3$, $R^4$, $R^5$ in each case denote an organic residue and wherein $R^1$, $R^2$, $R^3$, $R^4$, $R^5$ independently of one another preferably in each case contain one or more aryl residues with at most 20 carbon atoms or branched or linear alkyl residues, which independently of one another in each case have 1 to 20 carbon atoms. The residues $R^1$, $R^2$, $R^3$, $R^4$, $R^5$ can also be singly or multiply unsaturated.

Moreover, tungsten(VI)-oxoalcoholates $(WO(OR^1)(OR^2)(OR^3)(OR^4))$ are especially preferred, wherein the residues $R^1$, $R^2$, $R^3$, $R^4$ in each case denote an organic residue and preferably in each case independently of one another denote an aryl residue with at most 20 carbon atoms or branched or linear alkyl or (singly or multiply unsaturated) alkenyl residue with 1 to 20 carbon atoms.

Tungsten(VI)-oxoperoxo complexes $[(WO(O_2)L^1L^2)$ or $(WO(O_2)_2L^1L^2)]$ are also especially preferred, wherein $L^1$ and $L^2$ independently of one another denote alkoxy ligands $(OR^6)$ or amino ligands $(N(R^7)(R^8)(R^9))$. The residues $R^6$, $R^7$, $R^8$, $R^9$ are in this case organic residues, preferably independently of one another in each case aryl residues with at most 20 carbon atoms or linear or branched alkyl or (singly or multiply unsaturated) alkenyl residues with 1-20 carbon atoms. The ligands $L^1$ and $L^2$ can alternatively be in the form of a chelate ligand, i.e. linked together, as in 8-hydroxyquinoline for example.

Catalysts selected from the group consisting of vanadium (III) acetylacetonate, vanadyl(IV) acetylacetonate, vanadium (V) oxytriisopropoxide, ammonium metavanadate and oxoperoxotungsten(VI) complexes comprising one or more ligands in the form of 8-hydroxyquinoline are quite especially preferred for the method according to the invention.

The production of oxoperoxotungsten(VI) complexes comprising one or more ligands in the form of 8-hydroxyquinoline is described in DE 100 46 865 A1, cf. especially paragraphs [0057] to [0062].

In the method according to the invention, for the particular catalyst system, a person skilled in the art will modify the reaction conditions so as to ensure the stability of the alpha-bisabolol present in the reaction mixture. In particular, in this case the reaction temperatures, and ligands and solvents for modifying the Lewis acidity of the particular transition metal compound may be mentioned as parameters to be set by a person skilled in the art.

In the method according to the invention it is preferable for the mixture that was prepared or provided to contain 0.0001 to 1 mol, preferably 0.001 to 0.5 mol of transition metal per mol of farnesol, relative to the amount of farnesol present in the mixture that was prepared or provided.

According to the invention, the conversion of farnesol to nerolidol preferably takes place at a temperature in the range from 50 to 300° C., preferably in the range from 150 to 200° C., and/or the reaction is carried out at a pressure of less than 1000 mbar, preferably in the range from 0.1 to 500 mbar.

Typically, the nerolidol that forms during the reaction of farnesol is removed from the reaction mixture by rectification during and/or after the reaction.

The reaction can, according to the invention, be carried out both batchwise, and continuously or partially continuously.

In an especially preferred configuration of the method according to the invention, one or more catalysts for selective isomerization of farnesol to nerolidol in the presence of alpha-bisabolol are added to a mixture comprising alpha-bisabolol, farnesol and optionally further constituents. The resultant mixture is then heated and the nerolidol that forms is separated by distillation using a rectification column. Excellent results have been achieved in this way. For catalysts that are preferred in this case, reference may be made to the information given above.

The mixture that is provided or prepared according to the invention optionally contains one or more further constituents, which are selected for example from the group consisting of: nerolidol, elimination products of alpha-bisabolol, elimination products of farnesol, elimination products of nerolidol, etherification products of farnesol, further sesquiterpenes, further sesquiterpene alcohols, further rearrangement products of alpha-bisabolol, nerolidol and farnesol, other solvents. The elimination products of alpha-bisabolol are in particular bisabolenes. The elimination products of farnesol are in particular farnesenes. The etherification products of farnesol are in particular difarnesyl ethers. The sesquiterpene alcohols are in particular sesquiterpene alcohols from the group consisting of khusiol, germacradienol, elemol, eudesmol and beta-bisabolol.

Moreover, the composition of the mixture that is prepared or provided usually depends on the method by which the alpha-bisabolol and farnesol contained in the mixture were formed.

In a preferred variant, the mixture that is prepared or provided contains one or more solvents that are stable under the reaction conditions and do not have a negative influence on the catalytic activity of the catalyst. Suitable solvents are high-boiling solvents. High-boiling solvents that are advantageously used have in common that their boiling point is above that of alpha-bisabolol, which allows subsequent separation of alpha-bisabolol from the solvent by distillation. Preferred high-boiling solvents used are selected from the group consisting of:

ethers, e.g. polyethylene glycol ether or polypropylene glycol ether;
mono- and dihydric alcohols, e.g. palmityl alcohol, stearyl alcohol and diethylene glycol and triethylene glycol;
polyethylene glycols and polypropylene glycols;
sulfoxides, e.g. sulfolane; and
hydrocarbons, e.g. squalane or paraffin oils.

The amount of solvent used is preferably in the range from 5 to 100 wt % relative to the total weight of the mixture that is prepared or provided.

In the method according to the invention, the step of preparing the mixture preferably comprises the conversion of nerolidol to a mixture comprising alpha-bisabolol and farnesol. Preferably, a mixture is prepared comprising alpha-bisabolol, farnesol and optionally further constituents by one of the methods mentioned above, preferably by the method according to WO 2004/033401. Alternative methods of preparing alpha-bisabolol, especially those that start from nerolidol as educt, can also be used.

In the context of the method according to the invention, the step of preparing the mixture preferably comprises:
saponification of alpha-bisabolyl formate and farnesyl formate mixed together or
transesterification of alpha-bisabolyl formate and farnesyl formate mixed together with an alcohol.

In each case, a product mixture is formed comprising alpha-bisabolol and farnesol.

In a preferred variant of the method according to the invention, alpha-bisabolol and nerolidol are separated from one another during and/or after conversion of farnesol to nerolidol. Preferably, during and/or after conversion of farnesol to nerolidol, the nerolidol is separated by distillation from the mixture obtained by conversion of farnesol to nerolidol.

The desired product alpha-bisabolol is then preferably distilled overhead at a pressure in the range 0.1-5 mbar. This distillation is also batchwise or continuous, e.g. using a thin-film evaporator. The catalyst and optionally further constituents with a boiling point above the boiling point of alpha-bisabolol remain in the bottom product.

In an especially preferred variant of the method according to the invention, the following steps are carried out in the same reaction vessel:
preparing a mixture comprising
alpha-bisabolol;
farnesol;
one or more catalysts for selective isomerization of farnesol to nerolidol in the presence of alpha-bisabolol; and
optionally further constituents; and
converting farnesol to nerolidol in the mixture The preparation of a mixture comprising alpha-bisabolol and farnesol and the conversion of farnesol to nerolidol in the mixture take place in situ as a one-pot reaction without isolating the resultant mixture comprising alpha-bisabolol and farnesol. In this variant of the method according to the invention it is especially advantageous if the step of preparing the mixture in said reaction vessel comprises the transesterification of bisabolyl formate and farnesyl formate with an alcohol $R^{10}$—OH. The residue $R^{10}$ can be a C1-C6-alkyl residue, e.g. methyl, ethyl, propyl, cyclopropyl, 1-methylethyl, butyl, 1-methylpropyl, 2-methylpropyl, 1,1-dimethylethyl, pentyl, cyclopentyl, 1-methylbutyl, 2-methylbutyl, 3-methylbutyl, 2,2-dimethylpropyl, 1-ethylpropyl, hexyl, cyclohexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl. An alcohol with a C1-C3-alkyl residue, e.g. methyl, ethyl, propyl is preferably used. Ethanol is especially preferred.

Preferably, one, several or all of the catalysts for selective isomerization of farnesol to nerolidol in the presence of alpha-bisabolol are (i) dissolved or (ii) suspended in the mixture that is prepared or provided. The first case (i) represents a homogeneous catalysis, as catalyst and educts are in the same phase. The second case (ii) represents a heterogeneous catalysis, as the catalyst on the one hand and the educts on the other hand are in different phases. In case (ii), the catalyst preferably comprises a support. Supports are chemically inert substances that are suitable as a substrate and framework for a catalytically active substance, e.g. substances with large surface areas selected from the group consisting of activated charcoal, alumina, silica gel, kieselguhr, talc, kaolin, clay, silicates, or polymeric materials that are inert under the respective reaction conditions.

Another object of the present invention is the use of a catalyst comprising a compound of a transition metal of groups 5 to 8 of the periodic table, preferably a compound of a transition metal selected from the group consisting of vanadium, rhenium, tungsten, manganese, chromium, molybdenum and palladium for selective isomerization of farnesol to nerolidol in the presence of alpha-bisabolol. Regarding preferred embodiments of the catalyst to be used according to the invention, the statements made above in connection with the method according to the invention apply.

The invention is explained in more detail below on the basis of practical examples.

Example 1.1

Preparation of a Mixture Comprising Alpha-Bisabolyl Formate and Farnesol Formate A 2000-ml three-necked flask with reflux condenser and thermometer is charged with 264 g (1.2 mol) of (+/−)-nerolidol and 100 g hexane. Then a total of 92 g (2 mol) of formic acid is added dropwise within 60 minutes at a temperature in the range from 10 to 15° C. Then the reaction mixture is stirred for 20 hours at a temperature in the range from 10 to 15° C. After carrying out analysis by gas chromatography (GC) the reaction mixture obtained is worked up. For this, 500 g water is added to the reaction mixture, and then the organic phase is separated and washed with soda solution and water until neutral. After distilling-off the solvent, 300 g of crude product remained.

Results of GC analysis
alpha-bisabolyl formates: 38.9 wt %;
farnesyl formates 29.7 wt %
(total of the 4 isomers cis/cis; cis/trans; trans/cis; trans/trans)

Note:

Here and in the following examples, GC percentage areas were determined (without internal standard) and equated with the percentages by weight to a good approximation; an error that possibly arose is assessed as negligible.

Example 1.2

Preparation of a Mixture Comprising Alpha-Bisabolol and Farnesol

A 2000-ml three-necked flask with reflux condenser, dropping funnel and thermometer is charged with 300 g (0.8 mol) of a mixture prepared according to example 1.1 comprising alpha-bisabolyl formate and farnesyl formate and 400 g methanol and then 480 g of sodium hydroxide solution (10 wt %) is added within 15 min at a temperature of 20 to 40° C. Then stirring is continued for 2 hours at a temperature in the range from 30 to 40° C. After carrying out analysis by gas chromatography (GC), the reaction mixture obtained is worked up. For this, 400 g water and 200 g diethyl ether are added to the reaction mixture, and then the organic phase is separated and washed with water until neutral. After distilling-off the solvent, 259.2 g of crude product remained.

Results of GC analysis
alpha-bisabolol: 37.3%
farnesol: 28.9%
(total of the 4 isomers cis/cis; cis/trans; trans/cis; trans/trans)

This roughly corresponds to a molar ratio of alpha-bisabolol to farnesol of 1.3:1.

GC conditions:
Equipment: Agilent 6890; FID detector
Column: 20 m DB-WAX, 0.18 μm inside diameter, 0.18 μm film thickness
Carrier gas: hydrogen, 1.6 bar; split 1:50
Injector: 250° C. Detector: 300° C.
Temperature program: 60° C.; 8 K/min; 250° C.

By rectification on a column with 40 plates, the content of alpha-bisabolol was increased to 86 wt % and the content of farnesol was decreased to 7 wt %. This corresponds to a molar ratio of alpha-bisabolol to farnesol of 12.3:1.

Example 2

Preparation of a Mixture Comprising Alpha-Bisabolol and Farnesol and Conversion of Farnesol to Nerolidol in the Mixture (According to the Invention)

A 500-ml three-necked flask with a 15-plate distillation column, column head and thermometer is charged with 250 g of a mixture comprising 43 wt % alpha-bisabolol, 40 wt % farnesol (equivalent to 0.45 mol farnesol, molar ratio of alpha-bisabolol to farnesol=1.075) and 1.2 g of vanadyl(IV) acetylacetonate (equivalent to 4.5 mmol) and heated at a temperature in the range from 174 to 176° C. and a pressure of 25 mbar for 7 hours. From this reaction mixture, 119 g of a fraction comprising 76 wt % nerolidol, 7 wt % alpha-bisabolol and 7 wt % hydrocarbons distils over.

The reaction mixture that remains is then separated from the residue by simple distillation at 1 mbar. In this, 113 g of a fraction is distilled off overhead, which contains 81 wt % alpha-bisabolol and 0.7 wt % farnesol. This corresponds to a molar ratio of alpha-bisabolol to farnesol of 115:1.

Example 3

Preparation of a Mixture Comprising Alpha-Bisabolol and Farnesol and Conversion of Farnesol to Nerolidol in the Mixture (According to the Invention)

A 500-ml three-necked flask with a 15-plate distillation column, column head and thermometer is charged with 250 g of a mixture comprising 43 wt % alpha-bisabolol and 40 wt % farnesol (equivalent to 0.45 mol farnesol, molar ratio of alpha-bisabolol to farnesol=1.075) and 1.1 g of vanadium(V) oxytriisopropoxide (equivalent to 4.5 mmol) and heated at a temperature in the range from 172 to 176° C. and a pressure of 25 mbar for 7 hours. From this reaction mixture, 116 g of a fraction comprising 77 wt % nerolidol, 6 wt % alpha-bisabolol and 6 wt % hydrocarbons distils over.

The reaction mixture that remains is then separated from the residue by simple distillation at 1 mbar. In this, 119 g of a fraction is distilled off overhead, which contains 83 wt % alpha-bisabolol and 1.0 wt % farnesol. This corresponds to a molar ratio of alpha-bisabolol to farnesol of 83:1.

Example 4

Preparation of a Mixture Comprising Alpha-Bisabolol and Farnesol and Conversion of Farnesol to Nerolidol in the Mixture (According to the Invention)

A 500-ml three-necked flask with a 15-plate distillation column, column head and thermometer is charged with 250 g of a mixture comprising 43 wt % alpha-bisabolol and 40 wt % farnesol (equivalent to 0.45 mol farnesol, molar ratio of alpha-bisabolol to farnesol=1.075) and 1.6 g of vanadium(III) acetylacetonate (equivalent to 4.5 mmol) and heated at a temperature in the range from 172 to 176° C. and a pressure of 25 mbar for 7 hours. From this reaction mixture, 116 g of a fraction comprising 75 wt % nerolidol, 6 wt % alpha-bisabolol and 8 wt % hydrocarbons distils over.

The reaction mixture that remains is then separated from the residue by simple distillation at 1 mbar. In this, 107 g of a fraction is distilled off overhead, which contains 79 wt % alpha-bisabolol and 0.5 wt % farnesol. This corresponds to a molar ratio of alpha-bisabolol to farnesol of 158:1.

Example 5

Preparation of a Mixture Comprising Alpha-Bisabolol and Farnesol and Conversion of Farnesol to Nerolidol in the Mixture (According to the Invention)

A 500 ml three-necked flask with a 15-plate distillation column, column head and thermometer is charged with 250 g of a mixture comprising 43 wt % alpha-bisabolol and 40 wt % farnesol (equivalent to 0.45 mol farnesol, molar ratio of alpha-bisabolol to farnesol=1.075) and 0.5 g ammonium metavanadate (equivalent to 4.5 mmol) and heated at a temperature in the range from 173 to 176° C. and a pressure of 25 mbar for 7 hours. From this reaction mixture, 132 g of a fraction comprising 65 wt % nerolidol, 15 wt % alpha-bisabolol and 6 wt % hydrocarbons distils over.

The reaction mixture that remains is then separated from the residue by simple distillation at 1 mbar. In this, 102 g of a fraction is distilled off overhead, which contains 85 wt % alpha-bisabolol and 0.9 wt % farnesol. This corresponds to a molar ratio of alpha-bisabolol to farnesol of 94.5:1.

Example 6

Preparation of a Mixture Comprising Alpha-Bisabolol and Farnesol and Conversion of Farnesol to Nerolidol in the Mixture (According to the Invention)

In a 50-ml Erlenmeyer flask, 12.5 g of tungstic acid (tungsten(VI) oxide monohydrate; equivalent to 50 mmol) is suspended in 20 g hydrogen peroxide (30 wt %) and stirred for 6 hours at a temperature of 40° C. After filtration it is transferred to a test tube and finely divided solid is left to sediment overnight. 20 g of the solution above the solid sediment (equivalent to ~20 mmol) is transferred to 750 g of a mixture comprising 10 wt % hydrocarbons, 40 wt % alpha-bisabolol and 35 wt % farnesol (equivalent to 1.18 mol farnesol, molar ratio of alpha-bisabolol to farnesol=1.14) in a 2000-ml three-necked flask with a 15-plate distillation column, column head and thermometer and then a solution of 10 g of 8-hydroxyquinoline (69 mmol) in 20 g ethanol is added. Then a fraction comprising alcohol and 8-hydroxyquinoline is distilled off at reduced pressure.

Then the reaction mixture is heated for 5 hours at a bottom temperature in the range from 155 to 160° C. and a pressure of 14 mbar. 438 g of a fraction comprising 56 wt % nerolidol, 10 wt % alpha-bisabolol and 24 wt % hydrocarbons distilled over. 317 g of a material that has a content, determined by gas chromatography, of 77 wt % alpha-bisabolol and 1.5 wt % farnesol remained in the bottom of the reaction mixture. This corresponds to a molar ratio of alpha-bisabolol to farnesol of 51.3:1.

300 g of cyclohexane is added to the bottom of the reaction mixture, which is then filtered on talc. After removing the cyclohexane, by simple distillation of the bottom product on a distillation bridge, 263 g of a fraction comprising 81 wt % alpha-bisabolol, <0.1 wt % farnesol, 1.5 wt % nerolidol and 7 wt % hydrocarbons is obtained. This corresponds to a molar ratio of alpha-bisabolol to farnesol of >810:1.

Example 7

Preparation of a Mixture Comprising Alpha-Bisabolol and Farnesol and Conversion of Farnesol to Nerolidol in the Mixture in a One-Pot Reaction (According to the Invention)

A 2-liter three-necked flask with a 15-plate distillation column, column head and thermometer is charged with 1000 g of a mixture prepared according to example 1.1 comprising alpha-bisabolyl formate and farnesyl formate, and 276 g ethanol and 10 g tetraethyl titanate are added. Then first ethyl formate and then ethanol are distilled off at normal pressure.

In the three-necked flask, 887 g of a mixture is obtained comprising 13 wt % hydrocarbons, 40 wt % alpha-bisabolol and 30 wt % farnesol (equivalent to 1.2 mol farnesol, molar ratio of alpha-bisabolol to farnesol=1.33), to which 4.0 g of vanadyl(IV) acetylacetonate is then added and it is heated for 7 hours at a temperature in the range from 174 to 176° C. and a pressure of 25 mbar. From this reaction mixture, 296 g of a fraction comprising 71 wt % nerolidol and 12 wt % alpha-bisabolol distils over.

The transesterification of alpha-bisabolyl formate and farnesyl formate with ethanol to ethyl formate, alpha-bisabolol and farnesol and the subsequent catalytic reaction of farnesol in the presence of alpha-bisabol to nerolidol thus take place in situ as a one-pot reaction.

The reaction mixture that remains is then separated from the residue by simple distillation at 1 mbar. In this, 399 g of a fraction is obtained, which contains 74 wt % alpha-bisabolol and 1.4 wt % farnesol. This corresponds to a molar ratio of alpha-bisabolol to farnesol of 52.8:1.

What is claimed is:

1. A method of converting farnesol to nerolidol by isomerization in the presence of alpha-bisabolol comprising:
   providing or preparing a mixture comprising:
   alpha-bisabolol;
   farnesol; and
   one or more catalysts for selective isomerization of farnesol to nerolidol in the presence of alpha-bisabolol; and
   converting at least a portion of the farnesol to nerolidol.

2. The method according to claim 1, wherein the molar ratio of alpha-bisabolol to farnesol after farnesol has been converted to nerolidol is greater than the molar ratio of alpha-bisabolol to farnesol prior to when farnesol was converted to nerolidol.

3. The method according to claim 1, wherein the mixture has a molar ratio of alpha-bisabolol to farnesol in a range from 15:1 to 1:100.

4. The method according to claim 1, wherein the mixture has a molar ratio of alpha-bisabolol to farnesol in a range from 2:1 to 1:2.

5. The method according to claim 1, wherein after farnesol has been converted to nerolidol the molar ratio of alpha-bisabolol to farnesol is 30:1 or higher.

6. The method according to claim 1, wherein after farnesol has been converted to nerolidol the molar ratio of alpha-bisabolol to farnesol is 80:1 or higher.

7. The method according to claim 1, wherein after farnesol has been converted to nerolidol the molar ratio of alpha-bisabolol to farnesol is 100:1 or higher.

8. The method according to claim 1, wherein at least one of the catalysts for selective isomerization of farnesol to nerolidol in the presence of alpha-bisabolol comprises a compound of a transition metal of groups 5 to 8 of the periodic table.

9. The method according to claim 8, wherein at least one of the catalysts for selective isomerization of farnesol to nerolidol in the presence of alpha-bisabolol comprises a compound of a transition metal selected from the group consisting of vanadium, rhenium, tungsten, manganese, chromium, molybdenum and palladium.

10. The method according to claim 1, wherein at least one of the catalysts for selective isomerization of farnesol to nerolidol in the presence of alpha-bisabolol is selected from the group consisting of vanadic acid esters and vanadic acid ammonium salts thereof.

11. The method according to claim 10, wherein at least one of the catalysts for selective isomerization of farnesol to nerolidol in the presence of alpha-bisabolol is selected from the group consisting of vanadium(III) acetylacetonate, vanadyl (IV) acetylacetonate, vanadium(V) oxytriisopropoxide and ammonium metavanadate.

12. The method according to claim 1, wherein at least one of the catalysts for selective isomerization of farnesol to nerolidol in the presence of alpha-bisabolol is selected from the group consisting of chelates and organometallic compounds of the transition metals of groups 5 to 8 of the periodic table.

13. The method according to claim 12, wherein at least one of the catalysts for selective isomerization of farnesol to nerolidol in the presence of alpha-bisabolol is selected from the group consisting of chelates and organometallic compounds of the transition metals selected from the group consisting of vanadium, rhenium, tungsten, manganese, chromium, molybdenum and palladium.

14. The method according to claim 12, wherein at least one of the catalysts for selective isomerization of farnesol to nerolidol in the presence of alpha-bisabolol is selected from the group consisting of the group of oxoperoxotungsten (VI) complexes comprising one or more ligands in the form of 8-hydroxyquinoline.

15. The method according to claim 1, wherein the catalyst is a compound of a transition metal and the mixture contains 0.0001 to 1 mol of transition metal per mol of farnesol, relative to the amount of farnesol present in the mixture.

16. The method according to claim 1, wherein the catalyst is a compound of a transition metal and the mixture contains 0001 to 0.5 mol of transition metal per mol of farnesol, relative to the amount of farnesol present in the mixture.

17. The method according to claim 1, wherein the conversion of farnesol nerolidol is carried out at a temperature in the range from 50 to 300° C.

18. The method according to claim 1, wherein the conversion of farnesol to nerolidol is carried out at a temperature in the range from 150 to 200° C.

19. The method according to claim 1, wherein the conversion of farnesol to nerolidol is carried out at a pressure of less than 1000 mbar.

20. The method according to claim 1, wherein the conversion of farnesol to nerolidol is carried out at a pressure in the range from 0.1 to 500 mbar.

21. The method according to claim 1, wherein the mixture further comprises one or more of the constituents selected from the group consisting of nerolidol, elimination products of alpha-bisabolol, elimination products of farnesol, elimination products of nerolidol, etherification products of farnesol, sesquiterpenes, sesquiterpene alcohols, germacradienol, beta-bisabolol, and rearrangement products of alpha-bisabolol, nerolidol and farnesol.

22. The method according to claim 1 further comprising converting at least a portion of the nerolidol to a mixture comprising alpha-bisabolol and farnesol.

23. The method according to claim 1 further comprising separating at least a portion of the alpha-bisabolol and nerolidol from one another.

24. The method according to claim 1 further comprising separating by distillation at least a portion of the nerolidol from the mixture obtained by conversion of farnesol to nerolidol.

25. The method according to claim 1, wherein each step is carried out in the same reaction vessel.

26. The method according to claim 1, wherein providing or preparing a mixture comprises saponification of alpha-bisabolyl formate and farnesyl formate mixed together.

27. The method according to claim 1, wherein providing or preparing a mixture comprises transesterification of alpha-bisabolyl formate and farnesyl formate mixed together with an alcohol.

28. The method according to claim 1, wherein at least one of the catalysts is dissolved in the mixture.

29. The method according to claim 1, wherein at least one of the catalysts is suspended in the mixture.

30. A method of converting farnesol to nerolidol by isomerization in the presence of alpha-bisabolol comprising:
providing a mixture comprising:
alpha-bisabolol;
farnesol; and
a catalyst comprising a compound of a transition metal of groups 5 to 8 of the periodic table; and
converting at least a portion of the farnesol to nerolidol.

31. The method according to claim 30, wherein the catalyst selectively isomerizes farnesol to nerolidol in the presence of alpha-bisabolol;
wherein the mixture has a molar ratio of alpha-bisabolol to farnesol in a range from 2:1 to 1:2;
wherein after farnesol has been converted to nerolidol the molar ratio of alpha-bisabolol to farnesol is 100:1 or higher;
wherein the mixture contains 0.001 to 0.5 mol of transition metal per mol of farnesol, relative to the amount of farnesol present in the mixture;
wherein the conversion of farnesol to nerolidol is carried out at a temperature in the range from 150 to 200° C.; and
wherein the conversion of farnesol to nerolidol is carried out at a pressure in the range from 0.1 to 500 mbar.

* * * * *